(12) United States Patent
Kim et al.

(10) Patent No.: US 8,652,416 B2
(45) Date of Patent: Feb. 18, 2014

(54) ARTICLE FOR ASSAYING TARGET, COMPRISING SOLID SURFACE ON WHICH FIRST BINDING MEMBER, BLOCKING MATERIAL, AND SECOND BINDING MEMBER ARE IMMOBILIZED, AND USE THEREOF

(75) Inventors: Ji Won Kim, Suwon-si (KR); Beom Seok Lee, Hwaseong-si (KR); In Wook Kim, Seoul (KR); Kui Hyun Kim, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1008 days.

(21) Appl. No.: 12/579,484

(22) Filed: Oct. 15, 2009

(65) Prior Publication Data

US 2010/0159483 A1 Jun. 24, 2010

(30) Foreign Application Priority Data

Dec. 22, 2008 (KR) ........................ 10-2008-0131202

(51) Int. Cl.
*G01N 33/52* (2006.01)

(52) U.S. Cl.
USPC ........................................................ 422/426

(58) Field of Classification Search
None
See application file for complete search history.

(56) References Cited

U.S. PATENT DOCUMENTS

| 4,258,001 | A | * | 3/1981 | Pierce et al. ................. 422/400 |
| 4,517,288 | A | * | 5/1985 | Giegel et al. ....................... 435/5 |
| 4,731,326 | A | * | 3/1988 | Thompson et al. ........... 435/7.25 |
| 5,496,702 | A | * | 3/1996 | Bishop et al. .................. 435/7.9 |
| 6,429,026 | B1 | | 8/2002 | Pettersson et al. |
| 6,632,682 | B1 | | 10/2003 | Ziegelmaier |
| 7,157,049 | B2 | * | 1/2007 | Valencia et al. ............. 422/68.1 |
| 2004/0189311 | A1 | * | 9/2004 | Glezer et al. .................. 324/444 |

FOREIGN PATENT DOCUMENTS

EP 0238012 * 3/1987 ............. G01N 33/52

* cited by examiner

*Primary Examiner* — Ann Lam
(74) *Attorney, Agent, or Firm* — Sughrue Mion, PLLC

(57) ABSTRACT

Disclosed are an article for assaying a target, wherein the article includes a solid surface on which a first binding member, a blocking material, and a second binding member are immobilized, a method of manufacturing the article, and a method of detecting a target using the article.

19 Claims, 1 Drawing Sheet

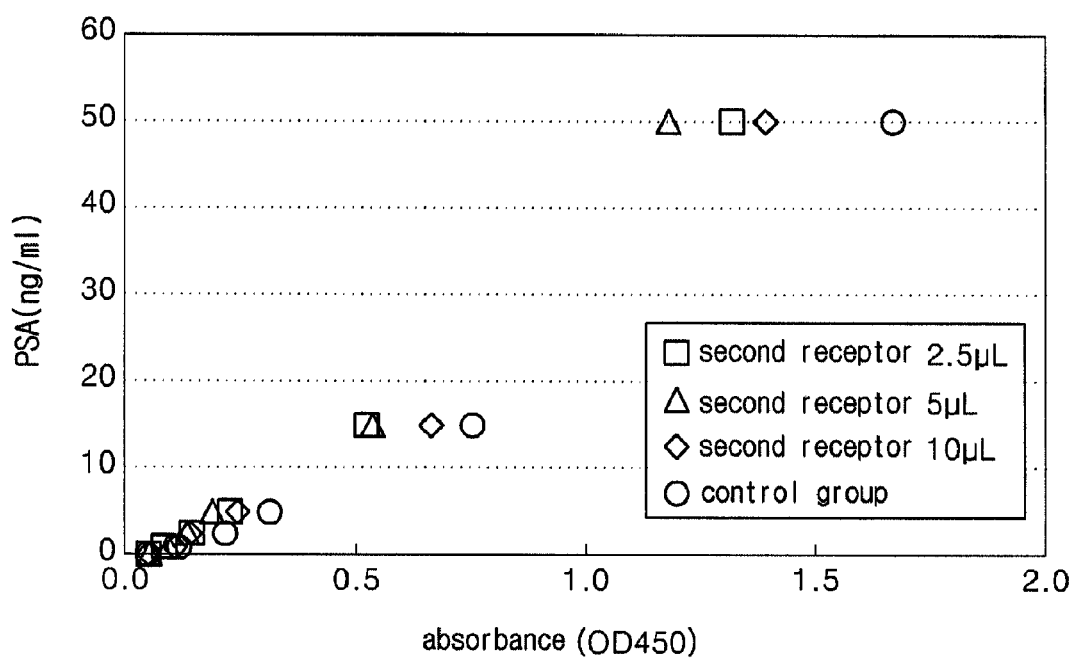

ARTICLE FOR ASSAYING TARGET, COMPRISING SOLID SURFACE ON WHICH FIRST BINDING MEMBER, BLOCKING MATERIAL, AND SECOND BINDING MEMBER ARE IMMOBILIZED, AND USE THEREOF

CROSS-REFERENCE TO RELATED APPLICATIONS

This application claims the benefit of Korean Patent Application No. 10-2008-0131202, filed on Dec. 22, 2008, in the Korean Intellectual Property Office, the disclosure of which is incorporated herein in its entirety by reference.

BACKGROUND

1. Field

One or more embodiments relate to a method of manufacturing an article or device for assaying a target, the article for assaying a target, and a method of detecting a target in a sample.

2. Description of the Related Art

Various target assay methods are known, for example, non-competitive target assay methods and competitive target assay methods. According to a non-competitive target assay method of detecting a target material in a sample, a first component that specifically binds to the target is immobilized to a solid substrate, the sample including the target to be detected is brought into contact with the first component to form a complex of the target and the first component, a labeled second component that can specifically bind to the target is brought into contact with the, and then a signal emitted from the complex including the first component, the target, and the second component is detected. The signal may be a signal emitted directly from a detectable label such as a fluorescent material of the labeled second component or a signal that is indirectly emitted by reacting an enzyme, such as horseradish peroxidase (HRP) or alkaline phosphatase (AP), of the labeled second component with a chromogenic substrate. This non-competitive target assay method may be an immunoassay.

According to a competitive target assay method of detecting a target in a sample, a first component that can specifically bind to the target is immobilized to a solid substrate, and in this state, in the presence of a labeled target or an analogue thereof, the sample including the target, which is not labeled, is added to the complex, and then signals emitted from the first component and the labeled target are detected. Thus, the more target is contained in the sample, the detected signal is weaker. The amount of the target is measured by comparing to a signal obtained using a reference solution containing a known concentration of the target.

In such conventional techniques, the second component and the labeled target are contained in a solution and are added to a reaction mixture during an assay reaction.

SUMMARY

One or more embodiments include a method of manufacturing an article for assaying a target, wherein the article includes a solid surface which has a first region and a second region; a first binding member which is immobilized on the first region of the solid surface, a blocking material which is immobilized on the second region of the solid surface, and a second binding member which is immobilized on the first region and the second region of the solid surface, wherein the first region is free of the second binding member and the second region is free of the first binding member.

One or more embodiments include a article for assaying a target, using an article, wherein the article includes a solid surface which has a first region and a second region; a first binding member which is immobilized on the first region of the solid surface, a blocking material which is immobilized on the second region of the solid surface, and a second binding member which is immobilized on the first region and the second region of the solid surface, wherein the first region is free of the second binding member and the second region is free of the first binding member.

One or more embodiments include a method of detecting a target using an article for assaying a target, wherein the article includes a solid surface which has a first region and a second region; a first binding member which is immobilized on the first region of the solid surface, a blocking material which is immobilized on the second region of the solid surface, and a second binding member which is immobilized on the first region and the second region of the solid surface, wherein the first region is free of the second binding member and the second region is free of the first binding member.

One or more embodiments include a microfluidic device containing a chamber which has a solid surface, the solid surface includes the immobilized first binding member, the blocking material, and the second binding member, described above.

Additional aspects will be set forth in part in the description which follows and, in part, will be apparent from the description, or may be learned by practice of the invention.

BRIEF DESCRIPTION OF THE DRAWINGS

These and/or other aspects will become apparent and more readily appreciated from the following description of the embodiments, taken in conjunction with FIG. 1 that shows absorbance with respect to the concentration of prostate specific antigen (PSA) at a wavelength of 450 nm.

DETAILED DESCRIPTION

Reference will now be made in detail to embodiments. In this regard, the embodiments may have different forms and should not be construed as being limited to the descriptions set forth herein. Accordingly, the embodiments are merely described below, by referring to the figures, to explain aspects of the present description.

An exemplary embodiment includes a method of manufacturing a article for assaying a target, wherein the method may include providing a solid surface having a first region and a second region; immobilizing a first binding member onto the first region of the solid surface, the first binding member being able to bind to the target; immobilizing a blocking material onto the second region of the solid surface; and immobilizing a second binding member onto the first and the second regions of the solid surface, the second binding member being labeled with an enzyme and being able to bind to the target, wherein the first region is free of the second binding member and the second region is free of the first binding member. The first binding member and the second binding member bind to a different binding site (e.g., different epitopes, different binding pockets, etc) of the target from each other.

The method may include the immobilizing of a first binding member onto a solid surface. For example, the solid surface may be a surface of a substrate that may be any one of plastic, silicon, glass, or a metal. The surface may be used as it is or modified or functionalized, for example in order to improve bonding of the binding members and a blocking material. The shape of the solid surface a flat surface, a wall of a well or a chamber, or a curved surface of a particle. The well may be a well disposed on a microwell plate or an individual well, and may also be space formed in a cartridge that may inserted or fit into a platform of a microfluidic apparatus. The platform may include all or part of structural elements of a microfluidic apparatus, or may provide a material or space that can be formed into the structural elements of a microfluidic apparatus. The platform may include a mounting portion that receives the cartridge. The mounting portion may be corrugated complementary to the cartridge so that the cartridge may be inserted into the mounting portion and immobilized. The cartridge may be coupled with the mounting portion of the microfluidic apparatus using various methods. For example, the coupling may be achieved by interlocking, fusion welding using supersonic waves, hot-melt bonding, or laser bonding. Examples of the solid substrate include a commercially available microtitration strip, a microplate, and UV-absorbed hypo fluorescent Maxisorb strip (Nunc, Roskilde, Denmark), etc.

The target may be an analyte. The target may be an antigen, an antibody, an enzyme, or an enzyme substrate. For example, the target may be a protein such as a prostate specific antigen (PSA), a thyroid stimulating hormone (TSH), thyroxine (3,4, 3′,5′-tetraiodothyronine) (T4), or testosterone, but is not limited thereto.

The first binding member and the second binding member are materials that specifically bind to the target. For example, the first binding member may be an antibody of an antigen, a receptor to a ligand, an enzyme catalyzing a substrate, or an enzyme that is inhibited by an enzyme inhibitor. The first binding member and the second binding member may be antibodies that bind to different sites (epitopes) of the target. The immobilizing may be achieved by using known methods. For example, the immobilizing may be achieved by covalent bonding or non-covalent bonding. For the immobilizing achieved by covalent bonding, a first binding member that is activated by a material such as N,N′-dicyclohexylcarbodiimide (DCC), 1-ethyl-3-(3-dimethylaminopropyl) carbodiimide hydrochloride (EDC), or N-hydroxysuccinimide (NHS) is reacted with an active group such as an amino group present in the solid surface or an amino group artificially introduced by surface modification in order to achieve the covalent bonding. For non-covalent bonding, the first binding member may be immobilized on the solid substrate by adsorption or capturing. The solid substrate may be activated by, for example, coating amino silane such as gamma-aminopropyltriethyoxysilane (GAPTES) on the solid substrate to introduce an amino group. According to an embodiment of the immobilizing the first binding member, the first binding member in a sodium bicarbonate buffer may be coated on the solid surface. The first binding member may also be immobilized on the solid surface indirectly. For example, a surface of the solid substrate is coated with streptavidin and then a biotinylated first binding member is linked thereto to be immobilized.

The method may also include the immobilizing of a blocking material onto a portion of the solid surface on which the first binding member is not immobilized. If a blocking material is immobilized on the portion of the solid substrate on which the first binding member is not immobilized, non-specific binding between the target and the solid substrate may be prevented or reduced. The blocking material may be a material that does not bind to the target. The blocking material may be, for example, bovine serum albumin (BSA) or casein. The immobilizing of the blocking material may be realized using known methods according to the type of the blocking material used, such as a protein, sugar, or a lipid. For example, a blocking material in a phosphate buffered saline (PBS) is added to a surface of the solid surface on which the first binding member is immobilized, and then incubated.

The method may also include the adding a solution containing a second binding member that is labeled with an enzyme and binds to the target, onto the solid surface on which the first binding member and the blocking material are immobilized. Then the surface may be dried to give an article which is suitable for assaying a target in a sample. The second binding member is a material that may specifically bind to the target. For example, the second binding member may be an antibody of an antigen, a receptor of a ligand, an enzyme catalyzing a substrate, or an enzyme which is inhibited by an enzyme inhibitor. The first binding member and the second binding member may bind to different sites of the target. For example, the first and second binding members may be antibodies.

A solution that can be used in immobilizing the second binding member may be, for example, 3-(N-morpholino)propanesulfonic acid (MOPS) or tris(hydroxymethyl)aminomethane (Tris) buffer. The drying may be lyophilizing, natural drying, or air-blowing drying. The enzyme may catalyze a reaction of a substrate, which results in emitting a signal that is detectable. The detectable signal may be an optical signal. The optical signal may be an absorbance signal, a chemical luminescence signal, or a fluorescent signal. For example, the enzyme may be horseradish peroxidase (HRP) or alkaline phosphatase (AP). The term "second binding member that is labeled with an enzyme" means that an enzyme is linked to the second binding member by covalent bonding or non-covalent bonding and the binding is maintained during an assay reaction, for example, in a washing process. The second binding member may be coated on the first binding member or the blocking material without use of other materials interposed between the second binding member and the first binding member or the blocking material. For example, such other materials may include a protein and/or a carbohydrate. According to this method, even without use of other materials, the second binding member is not non-specifically bound to a material that is not the target. Accordingly, the non-specific binding does not affect assay results of the target in a sample.

When the second binding member is coated on the first binding member and the blocking material and brought into contact with a liquid sample that contains the target, the target may bind to the second binding member in the liquid sample. In this regard, no incubation is necessary after a solution containing a second binding member is coated on the surface.

The concentration of the second binding member contained in the solution may be about 10 to about 40 times higher than a stoichiometric amount or a concentration that is desired to detect a target at a certain concentration in a sample. For example, the second binding member may be an antibody having a concentration in a range of about 17 µg/ml to about 68 µg/ml, when a target present in a sample at 0-30 ng/ml or higher. Herein, the term "concentration that is desired" refers to a concentration of the second binding member that is necessary to assay a target present in a sample at a certain minimum or maximum amount in assays. In conventional assaying reactions, a second binding member is usually highly diluted before use (for example, about 1,000 times to about 10,000 times), and thus, the second binding member is inclined to be unstable. The stability refers to the capability of the second binding member to maintain its binding to the target over time, temperatures, pressures, and chemical materials. Use and drying of the high-concentrated second binding member may lead to an increase in stability of the second binding member. The solution containing the second binding member used may have a volume in a range from about 2.5 µg to about 10 µg and the drying may be performed for about 10 minutes to about 30 minutes. In addition, the solution containing the second binding member may further include a stabilizer for the second binding member. Examples of the stabilizer include BSA, sucrose, trehalose, gelatin and casein, etc.

According to an embodiment of the method, the solid surface may be a well-shaped cartridge that may be coupled to a platform of a microfluidic apparatus. The platform may include all or part of structural elements of a microfluidic apparatus, or provides a material or space that can be formed into the structural elements of a microfluidic apparatus. The platform may include a mounting portion that receives the cartridge. The mounting portion may be corrugated complementary to the cartridge so that the cartridge is inserted or fit into the mounting portion and immobilized. Therefore, the method may further include coupling the cartridge having a surface of well on which a first binding member, a blocking material, and a second binding member are immobilized, to the mounting portion of the platform. The term "microfluidic apparatus" refers to an apparatus that includes an outlet and/or inlet that is connected to a micro channel and/or chamber and has about 1 nm to about 1000 µm of a cross section, that is, a diameter, a height, a width, or a depth. The platform may rotate around a rotation center, and may include channels and/or chambers in a radial direction from the rotation center. The coupling of the cartridge and the platform may be performed by interlocking, fusion welding using supersonic waves, hot-melt bonding, or laser bonding. For example, the cartridge may be inserted into the mounting portion of the platform so that the cartridge and the mounting portion of the platform are interlocked, or the cartridge and the mounting portion of the platform which are interlocked may be bonded by fusion welding using supersonic waves, hot-melt bonding, or laser bonding. Alternatively, the cartridge may have a shape which fits the mounting portion (e.g., chamber or channel) and, thus, is coupled to the microfluidic apparatus by inserting the cartridge into the mounting portion. The microfluidic apparatus may be used as a lab-on-a-chip or a lab-on-a-disc. Thus apparatus may include a plurality of cartridges each have a first binding member, a blocking material, and a second binding member are immobilized on the surface of the well of the cartridges according to embodiments described herein. A plurality of the cartridges may be simultaneously fabricated and simultaneously linked to the platform by aligning the portions of the platform which will be coupled to a cartridge to respective cartridges arranged on a support and bonding the cartridges to the platform. The support may be a flat panel which links a plurality of cartridges each other. The cartridge may be coupled to the micro fluidic apparatus in a way that an opening of the well of the cartridge is in fluid communicate with a fluid in the apparatus.

The coupling of a cartridge to a mounting portion of a platform may be carried out as a part of an assay apparatus fabrication process. For example, during an assay apparatus fabrication process which includes bonding two plates together to form a space therebetween, a platform coupled to the cartridge is used as one of the plates and coupled to a plate, thereby forming a reaction chamber defined by the well of the cartridge and the plate. The resultant article may be a microfluidic apparatus. The coupling of the surface of the solid substrate and the plate may be performed using known methods such as an ultraviolet (UV) bonding method. The microfluidic apparatus may include a reaction chamber in which the first binding member, the blocking material and the second binding member are immobilized on its inner wall, and may not include a chamber which contains only the second binding member.

Another exemplary embodiment provides an article or device for assaying a target, wherein the article or device includes: a first binding member immobilized on a first region of a surface of a solid substrate; a blocking material immobilized on a second region of the surface, where the first binding member is not immobilized; and a second binding member that is immobilized on the first region and the second regions where the first binding member or the blocking material are immobilized, wherein the first binding member and the second binding member bind to the target, and wherein the second binding member is labeled with an enzyme.

The article may be manufactured by using the exemplary method as described above. The solid substrate may be of a flat panel, a well, a chamber, or a particle. The article may be a microfluidic apparatus. In this case, the solid substrate on which the first binding member, the blocking material, and the second binding member labeled with an enzyme are immobilized may constitute a surface of a reaction chamber of a microfluidic apparatus, for example, a bottom surface of the reaction chamber of the microfluidic apparatus. The reaction chamber may be formed using, for example the exemplary method as described above.

Another exemplary embodiment provides a method of detecting a target in a sample, wherein the method includes: bringing a liquid sample including the target into contact with the surface of the solid substrate of the article; washing the surface of the solid substrate; bringing the washed surface of the solid substrate into contact with a substrate of the enzyme in a liquid medium; and measuring a signal emitted from a resultant of an enzymatic reaction of the substrate in the liquid medium.

The detection method may include bringing of a liquid sample including the target into contact with the surface of the solid substrate of the article. The article is the same as described above. The sample may be any material that includes the target. For example, the sample may be a biological sample such as blood, saliva, tissues, cells or a biopsy sample. The sample may be contained in proper buffer such as water or PBS buffer. The contact condition may be appropriately selected according to bonding reactions between the first binding member and the second binding member and the target. For example, bringing into contact may be performed at a temperature in a range of about 0° C. to about 40° C. at a pH in a range of about 3 to about 8. In addition, the first binding member and the second binding member may be antibodies and bringing into contact may be performed at a temperature in a range of about 0° C. to about 40° C. at a pH in a range of about 3 to about 8. By bringing into contact, the target in the liquid sample is linked to the first binding member and the second binding member. As a result of bringing into contact, a composite in which the first binding member is linked to the second binding member via the target, that is, a composite having a structure of first binding member-target-second binding member is formed.

The detection method may also include the washing of the surface of the solid substrate. The washing is performed to remove a material that is not linked to or non-specifically linked to the first binding member and/or the second binding member from the sample. A washing solution may be a washing solution that is used in known target assay methods, such as in immunoassay. The washing solution may be PBS buffer. In addition, washing conditions such as the number of washing may be appropriately designed by a person skilled in the art according to the first binding member, the target, and the second binding member. The washing conditions may be any condition under which the composite of first binding member-target-second binding member is not separated from the solid substrate and a reactant that is not linked or a article that is non-specifically linked are removed.

The detection method may also include bringing of the washed surface of the solid substrate into contact with a substrate of the enzyme in a liquid medium. For example, the enzyme may be horseradish peroxidase (HRP), beta-galactosidase, glucuronidase and, phosphatase (AP), or the like. In addition, the substrate may be a chromogenic (for example, 3,3-diaminobenzidin (DAB), 3,3',5,5'-tetramethylbenzidine (TMB), 2,2'-azino-bis(3-ethylbenzthiazoline)-6-sulphonic acid (ABTS), para-nitrophenylphosphate (pNPP), 5-bromo-4-chloro-3-indolyl phosphate (BCIP) or X-gal), or a chemical luminescence substrate (for example, luminol and acridine). The liquid medium may be suitable for the selected enzyme reaction. The liquid medium may be appropriately selected by a person skilled in the art according to the selected enzyme. For example, the liquid medium may be PBS or Tris buffer. The contact conditions may also be selected by a person skilled in the art according to the selected enzyme.

The detection method may also include measuring of a signal emitted from a article of an enzymatic reaction of the substrate in the liquid medium. The signal may be a measurement of the target in the liquid sample. The signal may be measured using an optical signal measuring instrument such as a spectroscope. The optical signal to be measured may have a varying wavelength according to the selected enzyme and substrate. For example, the wavelength may be about 405 nm, about 450 nm, or about 630 nm, but is not limited thereto.

One or more embodiments will be described in further detail with reference to the following examples. These examples are for illustrative purposes only and are not intended to limit the scope of the one or more embodiments.

EXAMPLE

Manufacture of Substrate on which First Binding Member, Blocking Material and Second Binding Member are Immobilized and Detection of Target Using the Resultant Substrate (1) Immobilization of First Binding Member A first binding member was immobilized on a solid substrate by physical adsorption. A mouse anti-PSA IgG antibody (Fujirebio Diagnostics, Malvern, USA) that constitutes the first binding member was coated on a well formed of polystyrene that is used for a lab-on-a-disc (LOD). The coating was performed by adding a mouse anti-PSA IgG antibody in a PBS buffer (pH 7.4) to the well and culturing the resultant well at a temperature of 4° C. overnight. In this process, the amount of mouse anti-PSA IgG antibody was 830 ng per well.

Then, 300 µl of BSA 1% in a PBS buffer (pH 7.4) solution was added to the well and then incubated at a temperature of 37° C. for 2 hours. Then, a supernatant is removed and then a drying process was performed at a temperature of 25° C. for 30 minutes.

(2) Immobilization of Second Binding Member that is Labeled with Enzyme

A solution containing a second binding member was added to the well and then a drying process was performed thereon. A mouse anti-PSA IgG-HRP (Fujirebio Diagnostics, Malvern, USA) was used as the second binding member. The second binding member was linked to PSA on other sites at which the first binding member was not linked.

A solution including 170 ng of a mouse anti-PSA IgG-HRP, and BSA that constitutes a stabilizer in MOPS (3-morpholinopropanesulfonic acid) buffer (pH6.5) was added in amounts of 2.5 µl, 5 µl and 10 µl respectively to the well on which the first binding member and the blocking material are immobilized, manufactured in (1), and then the resultant well was dried. The drying was performed by placing the resultant well in a desiccator at room temperature for one hour.

(3) Detection of Target

A PSA-containing sample was added to the well on which the first binding member, the blocking material and the second binding member were immobilized, manufactured in (2). PSA was used as a target. Then, an HRP substrate was added thereto. Absorbance of the reaction results was measured.

A known concentration of PSA was added to a serum to produce a known concentration of PSA-containing serum (reference sample). 46 µl of serum containing various known concentrations of PSA was added to the well on which the first binding member, the blocking material, and the second binding member were immobilized, manufactured in (2), and then the resultant well was incubated at a temperature of 37° C. for 9 minutes. The reaction mixture was washed with 300 µl of a washing buffer (PBS, Tween-20) once. Then, 100 µl of TMB solution was added to the well and incubated at a temperature of 37° C. for 6 minutes. Then, 50 µl of 1M $H_2SO_4$ was added thereto to stop the reaction. Absorbance of the reaction mixture was measured at a wavelength of 450 nm by using a VERSAmax device manufactured by Molecular Device Co.

For a control group, the concentration of PSA was measured using a conventional method. According to the conventional method, a first binding member was immobilized on a well in the same method as described in (1), and a second binding member was directly added thereto during assay reactions instead of using of the method described in (2) in which the second binding member was immobilized. Specifically, 46 µl of PSA-containing sample was added to the well on which the first binding member and the blocking material are immobilized, manufactured in (1), and then immediately, 100 µl of a solution including 170 ng of mouse anti-PSA IgG-HRP, and BSA as a stabilizer in MOPS buffer (pH6.5) were added thereto. Then, the target detection process as described above was performed.

The results are shown in Table 1.

TABLE 1

| PSA Concentration (ng/ml) | Control Group | Experimental Group | | |
|---|---|---|---|---|
| | | 2.5 µl | 5 µl | 10 µl |
| 0 | 0.044 | 0.050 | 0.049 | 0.047 |
| 0.8 | 0.120 | 0.089 | 0.091 | 0.105 |
| 2.5 | 0.214 | 0.142 | 0.131 | 0.137 |
| 5 | 0.311 | 0.228 | 0.188 | 0.242 |
| 15 | 0.753 | 0.522 | 0.535 | 0.660 |
| 20 | 1.666 | 1.318 | 1.179 | 1.390 |
| $R^2$ | 0.9998 | 1 | 0.9988 | 0.9987 |

Table 1 shows absorbance measured at a wavelength of 450 nm according to the concentration of PSA and a relationship between the concentration and absorbance. Referring to Table 1, results of Experimental Group in which PSA is measured using the well used in Example 1 was similar to results of Control group, and thus it can be seen that the correlation of Experimental Group is high. In Table 1, $R^2$ is a figure representing correlation of regression equation. FIG. 1 is a diagram of absorbance with respect to the concentration of PSA at a wavelength of 450 nm.

By referring to such results compared to conventional methods, it can be seen that a target can be more precisely detected by using a solid substrate on which a first binding member, a blocking material and a second binding member are immobilized. The above results indicate that a separate chamber including the second binding member, as used in conventional methods, is not required for obtaining accurate assay results. Thus, the assay device and method can be simplified. Specifically, if the article is a microfluidic apparatus, as a separate chamber including the second binding member is not needed, a structure (e.g., valve) that controls flow of the second binding member into or out of a chamber is also not needed. For example, at least three valves, including valves that control flow of the second binding member into and out of a second binding member chamber and a valve that controls flow of the second binding member into a reaction chamber, are also not needed.

As described above, by using a method of manufacturing a device for assaying a target according to an exemplary embodiment, the device can be efficiently manufactured.

Also, by using the device for assaying a target according to another exemplary embodiment, the device can be easily manufactured and the target can be efficiently assayed.

Also, by using a method of detecting a target in a sample according to another exemplary embodiment, the target in the sample can be easily, efficiently detected.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A method of manufacturing an article for assaying a target, the method comprising:
   providing a substrate having a solid surface, said surface including a first region and a second region;
   immobilizing a first binding member onto the first region of the surface, said first binding member is capable of binding to the target;
   applying a solution containing a second binding member to the surface where the first binding member and a blocking material are immobilized,
   wherein the second binding member is labeled with an enzyme and is capable to bind to the target; and
   drying the surface.

2. The method of claim 1, wherein the first binding member and the second binding member are antibodies which bind to different sites of the target.

3. The method of claim 1, wherein the immobilizing of the first binding member is performed by coating a solution containing the first binding member on the first region of the surface, wherein said solution comprises a phosphate buffered saline or a sodium bicarbonate buffer.

4. The method of claim 1, wherein the blocking material is bovine serum albumin or casein.

5. The method of claim 1, wherein the immobilizing of the blocking material is performed by adding the blocking material in a phosphate buffered saline to the surface and incubated.

6. The method of claim 1, wherein the enzyme is horseradish peroxidase or alkaline phosphatase.

7. The method of claim 1, wherein a shape of the solid substrate is a flat panel, a well, a chamber, or a particle.

8. The method of claim 1, wherein the second binding member is directly coated to the first and second regions of the surface.

9. The method of claim 1, wherein the concentration of the second binding member is about ten time to about 40 times higher than a stoichiometric amount.

10. The method of claim 1, wherein the substrate is a cartridge that has a well formed therein and has a shape to be inserted to a microfluidic apparatus platform.

11. The method of claim 10, further comprising coupling the cartridge to a mounting portion of the platform, wherein the first binding member, the blocking material, and the second binding member are immobilized on an inner surface of the well.

12. The method of claim 11, wherein the platform rotates about a rotation center and comprises a channel and a chamber arranged in a radial direction from the rotation center.

13. The method of claim 11, wherein the coupling of the cartridge and the platform is performed by fusion welding using supersonic waves, hot-melt bonding, or laser bonding.

14. The method of claim 11, further comprising coupling the platform coupled to the cartridge with a plate, thereby forming a reaction chamber defined by the well of the cartridge and the plate, and wherein the article is a microfluidic apparatus.

15. An article for assaying a target, the article comprising:
   a substrate having a solid surface, said surface including a first region and a second region;
   a first binding member immobilized on the first region of the surface, said first binding member being capable of binding to the target;
   a blocking material immobilized on the second region of the surface; and
   a second binding member immobilized on the first binding member in the first region of the surface and on the blocking material in the second region of the surface, said second binding member being capable of binding to the target and being labeled with an enzyme,
   wherein the first region is free of the blocking material and the second region is free of the first binding member.

16. The article of claim 15, wherein the substrate is a flat panel, a well, a chamber or a particle.

17. A method of detecting a target in a sample, the method comprising:
   bringing the sample in a liquid form into contact with a solid surface of an article, said article comprising
   a substrate having the solid surface, said surface including a first region and a second region;
   a first binding member immobilized on the first region of the surface, said first binding member being capable of binding to the target;
   a blocking material immobilized on the second region of the surface; and
   a second binding member immobilized on the first binding member in the first region of the surface and on the blocking material in the second region of the surface, said second binding member being capable of binding to the target and being labeled with an enzyme,
   wherein the first region is free of the blocking material and the second region is free of the first binding member;
   washing the surface;
   bringing the washed surface into contact with a substrate of the enzyme in a liquid medium; and
   measuring a signal emitted from a resultant of an enzymatic reaction of the substrate in the liquid medium.

18. The method of claim 17, wherein the enzyme is horseradish peroxidase or alkaline phosphatase.

19. The method of claim 17, wherein the substrate is selected from the group consisting of 3,3-diaminobenzidin (DAB), 3,3',5,5'-tetramethylbenzidine (TMB), 2,2'-azino-bis (3-ethylbenzthiazoline)-6-sulphonic acid (ABTS), para-nitrophenylphosphate (pNPP), 5-bromo-4-chloro-3-indolyl phosphate (BCIP), luminol and acridine.

* * * * *